US00PP15076P2

(12) United States Plant Patent
Carruth

(10) Patent No.: US PP15,076 P2
(45) Date of Patent: Aug. 10, 2004

(54) FLORIBUNDA ROSE PLANT NAMED 'WEKSCEMALA'

(50) Latin Name: *Rosa hybrida*
Varietal Denomination: WEKscemala

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 10/719,930

(22) Filed: Nov. 20, 2003

(51) Int. Cl.[7] ..... A01H 5/00
(52) U.S. Cl. ..... Plt./143
(58) Field of Search ..... Plt./143

*Primary Examiner*—Anne Marie Grunberg
*Assistant Examiner*—Annette H Para
(74) *Attorney, Agent, or Firm*—Christie, Parker & Hale, LLP

(57) ABSTRACT

A new variety of Floribunda rose suitable for garden decoration, having flowers of yellow blushed orange-red coloration.

1 Drawing Sheet

Classification: The present invention relates to a new *Rosa hybrida* plant.

Variety denomination: The new plant has the varietal denomination 'WEKscemala'.

BACKGROUND OF THE INVENTION

This invention relates to a new and distinct variety of Floribunda Rose. It has as its seed parent the variety known as 'WEKplapep' (U.S. Plant Pat. No. 10,126) and as its pollen parent the variety known as 'MEIcauf' (U.S. Plant Pat. No. 7,718).

SUMMARY OF THE INVENTION

Among the features which distinguish the new variety from other presently available and commercial rose cultivars known to the inventor are the following combination of characteristics: its many stipitate glands on the surface of the bud, its colors that blush and intensity from the newly opened stage to the three day old flower, its red suffusion on the style and its rough rachis with many stipitate glands and some small prickles. The plant has a moderately compact upright growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKscemala' may be asexually propagated by budding and grafting. The budding and grafting successfully occurred on the plant/rootstock *Rosa hybrida* cv. 'Dr. Huey'.

COMPARISON WITH PARENTS

The new rose may be distinguished from its seed parent, 'WEKplapep' by the following combination of characteristics: whereas 'WEKscemala' bears flowers of yellow blushed orange-red coloration with double petalage (about 22 to 27 petals), 'WEKplapep' bears flowers of striped red and white coloration with significantly heavier petalage (about 31 to 36 petals). The seed parent bears flowers with a strong damask and spicy fragrance, whereas the new variety bears flowers with a significantly lighter, slight tea fragrance.

The new variety may be distinguished from its pollen parent, 'MEIcauf' by the following combination of characteristics: whereas 'WEKscemala' bears medium sized flowers (about 8.4 to about 11.3 cm. in diameter) of yellow blushed orange-red coloration, 'MEIcauf' bears significantly larger flowers of even red coloration. The new variety is classified as a floribunda rose with a moderately compact upright medium height growing habit, whereas the pollen parent is classified as a hybrid tea rose with a significantly taller upright growing habit.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of November. Phenotypic expression may vary with environmental, cultural and climatic conditions, as well as differences in conditions of light and soil.

FLOWER

The new variety sometimes bears its flowers singly, sometimes in clusters of three to four or more per stem. Flowers may be borne in regular rounded clusters on strong somewhat short stems (about 23 to about 35 cm). Outdoors, the plant blooms abundantly and nearly continuously during the growing season. The flowers have a slight tea fragrance.

BUD

The peduncle is about 4.0 to about 7.5 cm. in length, of average caliper (about 0.2 to about 0.3 cm. in diameter), and usually erect. It is moderately rough, with numerous stipitate glands. Peduncle color is between 144A and 147A often moderately suffused, especially on the side exposed to the sun, with between 183B and 187C.

Before the calyx breaks, the bud is about 1.1 to about 1.8 cm. in diameter at the widest point, about 1.5 to about 2.3 cm. in length, and pointed in shape. The surface of the bud bears few foliaceous appendages and many stipitate glands, usually with slender mostly entire but sometimes somewhat cut foliaceous parts extending beyond the tip of the bud about ¼ or more of its length. Bud color is between 146B and 137A sometimes moderately suffused, especially on the side exposed to the sun, with between 183B and 187A.

The sepals are about 2.6 to about 3.6 cm. in length and about 0.7 to about 1.1 cm. in width at the widest point. The outer surface color of the sepal is between 146B and 137A sometimes moderately suffused, especially on the side exposed to the sun, with between 183B and 187A. The inner surface color of the sepal is between 147A and 145A and covered with fine wooly tomentum; sepal margins are lined with many stipitate glands.

As the petals open (after the calyx breaks), the bud is about 1.9 to about 2.5 cm. in diameter at the widest point, about 2.2 to about 2.9 cm. in length, and moderately ovoid in form. The color of the under surfaces of the newly opened petals is between 7A and 4A usually blushed with between 33C and 34B. There is no visible change in coloration at the point where the petal attaches. On the upper surfaces of the newly opened petals, at the point where the petal attaches, there is a somewhat large zone of between 7A and 4A that gradually suffuses from the center of the petal with between 30B and 32B, usually blushed with between 33B and 34A near the petal edge.

BLOOM

When fully open, the bloom ranges from about 8.4 to about 11.3 cm. in diameter. Petalage is double with about 22 to 27 petals and about 0 to 2 petaloids irregularly arranged. When partially open, the bloom form is moderately cupped to somewhat high centered, and the petals are somewhat tightly spiraled to moderately cupped with petal edges slightly reflexed outward. When fully open, the bloom form is more cupped, and the petals are loosely cupped and sometimes somewhat undulated with petal edges moderately reflexed outward.

PETALS

The substance of the petals is moderately heavy to somewhat leathery and of medium thickness, with upper surfaces moderately shiny and under surfaces somewhat shiny to matte. The outer petals are broadly rounded in shape with rounded apices. The inner petals are moderately obovate in shape with rounded apices. The petals are about 3.5 to about 4.7 cm. in length and about 2.8 to about 4.9 cm. in width at the widest point. Petal margins are entire.

NEWLY OPENED FLOWER

On the under surface of the outer petals, at the point where the petal attaches, there is a somewhat large zone of between 7A and 5C that gradually suffuses toward the center of the petal to between 4D and 5C, sometimes moderately blushed with between 43C and 48B. On the upper surface of the outer petals, at the point where the petal attaches, there is a somewhat large zone of between 7A and 4A that gradually suffuses to the center of the petal to between 4D and 5C, usually heavily blushed with between 41B and 33B.

The under surface color of the intermediate and inner petals is between 12B and 5C usually heavily blushed with between 44C and 33B. There is no visible change in coloration at the point where the petal attaches. On the upper surface of the intermediate and inner petals, at the point where the petal attaches, there is a somewhat large zone of between 7A and 4A that gradually suffuses toward the center of the petal to between 4C and 5C, usually heavily blushed with between 33A and 33B. The blushed section of the petals is sometimes irregularly striped and flecked with color ranging from between 33D and 33C to between 5D and 5C.

The general tonality of the newly opened flower is between 4C and 5C, usually heavily blushed with between 33A and 33B and sometimes irregularly striped and flecked with color ranging from between 33D and 33C to between 5D and 5C.

THREE-DAY-OLD FLOWER

On the under surface of the outer, intermediate and inner petals, at the point where the petal attaches, there is a somewhat large zone of between 6D and 5D that gradually suffuses toward the center of the petal to between 11D and 8D, often moderately blushed with between 53B and 48B.

On the upper surface of the outer, intermediate and inner petals, at the point where the petal attaches, there is a somewhat large zone of between 6D and 5D that gradually suffuses toward the center of the petal to between 4D and 5C, usually heavily blushed with between 42A and 46A and sometimes irregularly striped and flecked with color ranging from between 36C and 40D to between 4D and 5C.

The general tonality of the three-day-old flower is between 4D and 5C, usually heavily blushed with between 42A and 46A and sometimes irregularly striped and flecked with color ranging from between 36C and 40D to between 4D and 5C.

On the spent bloom, the petals usually persist, fading to between 43C and 48B and then eventually drop off cleanly.

In November in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are average in number (average about 105) and are arranged regularly about the pistils; a few are mixed with petaloids. The filaments are of somewhat short to medium length (about 0.3 to about 0.8 cm.), most with anthers. Filaments are between 13A and 14A in color. The anthers are small for the class and all open approximately at the same time. Anther color is between 21C and 12D when immature and between 200C and 163C at maturity. Pollen is somewhat abundant.

FEMALE REPRODUCTIVE ORGANS

Pistils vary in number (average about 75). The styles are moderately even, average in length (about 0.5 to about 0.7 cm.), somewhat thin to average in caliper, and loosely bunched to somewhat separated. Stigma color is between 5C and 8B. Style color is between 1C and 151B often heavily suffused near the top with between 53A and 53B. Ovaries are usually all enclosed in the calyx.

Hips have not been observed on this variety when grown in Upland, Calif.

FOLIAGE

The compound leaves are usually comprised of three to seven or more leaflets and are borne abundantly. The seven-leaflet leaves are about 11.4 to about 16.1 cm. in length and about 6.2 to about 12.3 cm. in width at the widest point, heavy to moderately crisp in texture, and moderately glossy in finish. The terminal leaflets are about 3.4 to about 6.3 cm. in length and about 2.0 to about 4.1 cm. in width at the widest point, shaped broadly oval to somewhat ovate with acute to somewhat acuminate apices and moderately acute to somewhat rounded bases. Their margins are simply serrate.

The upper surface color of the mature leaf is between 147A and 137B. The under surface color of the mature leaf is between 147B and 137C. The upper and under surface color of the young leaf is between 137C and 146A, usually heavily suffused with between 183A and 187A.

The rachis is somewhat light to average in caliper and rough. The upper side is shallowly grooved with very few hairs and stipitate glands on the edges of the grooves. The under side of the rachis is rough with many stipitate glands and some small prickles. The rachis color is between 145B and 146A.

The stipules are about 1.4 to about 2.1 cm. in length and moderately wide (about 0.6 to about 1.0 cm.) with medium length straight points that usually turn out at an angle of more than 45 degrees and often recurve toward the stem. The stipules color is between 137B and 146C sometimes suffused with between 187B and 183B.

The petiole is about 0.3 to about 1.0 cm. in length and about 0.1 to about 0.2 cm in diameter at the widest point. The petiole color is between 145B and 146A.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a moderately compact upright medium height growing habit (about 109 to about 121 cm. in height and about 62 to about 76 cm. spread at the widest point), with full branching. It displays moderately vigorous growth and the canes are of somewhat light to medium caliper for the class.

The color of the major stems is between 148A and 152A. They bear several large prickles that are about 0.5 to about 0.7 cm. in length. The large prickles are almost straight and angled slightly downward with a somewhat short oval to moderately rounded base; prickle color is between 165A and 177B. The major stem bears several small prickles of similar shape and coloration.

The color of the branches is between 146B and 147A often heavily suffused with between 187B and 183B. They bear many large prickles which are of similar size and shape to the large prickles on the major stems; prickle color is between 147A and 146B often heavily suffused with between 187B and 183B. The branches bear several small prickles of similar shape and coloration.

The color of the new shoots is between 146B and 147A often heavily suffused with between 187B and 183B. They bear many large prickles which are of similar size and shape to the large prickles on the major stems; prickle color is between 147A and 146B often heavily suffused with between 187B and 183B. The shoots bear several small prickles of similar shape and coloration.

I claim:

1. A new and distinct Floribunda rose plant of the variety substantially as described and illustrated herein.

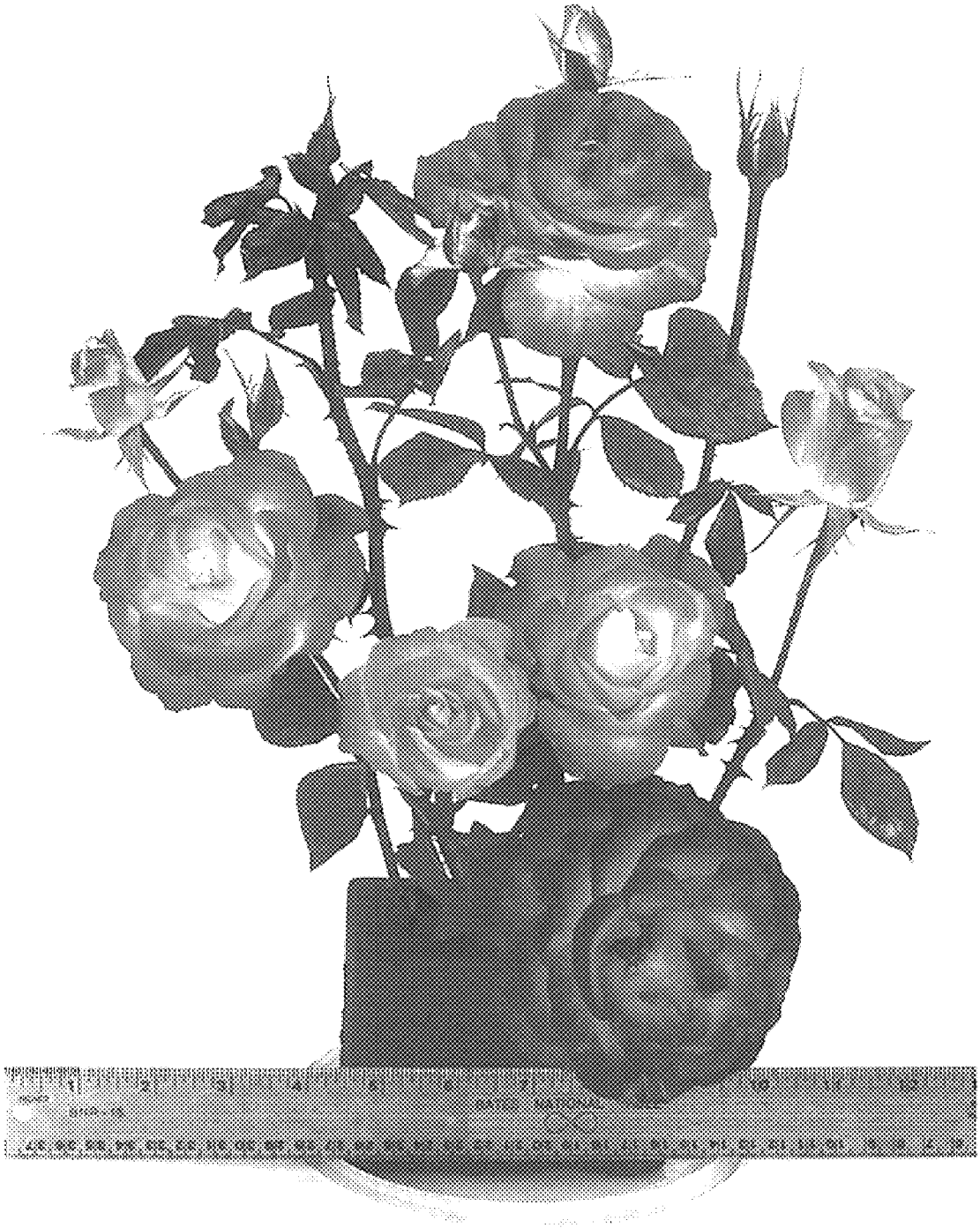

* * * * *